United States Patent [19]

Sick

[11] 4,248,537
[45] Feb. 3, 1981

[54] OPTICAL APPARATUS FOR DETERMINING THE LIGHT EXIT ANGLE FROM A MATERIAL STRIP ILLUMINATED BY A LIGHT BEAD

[75] Inventor: Erwin Sick, Icking, Fed. Rep. of Germany

[73] Assignee: Erwin Sick GmbH Optik-Elektronik, Fed. Rep. of Germany

[21] Appl. No.: 972,301

[22] Filed: Dec. 22, 1978

[30] Foreign Application Priority Data

Jan. 4, 1978 [DE] Fed. Rep. of Germany ..... 28003512

[51] Int. Cl.$^3$ ..................... G01N 21/84; G01N 21/88
[52] U.S. Cl. ................................... 356/431; 250/563
[58] Field of Search ................ 250/562, 563; 356/430, 356/431

[56] References Cited

U.S. PATENT DOCUMENTS

| | | | |
|---|---|---|---|
| 3,198,951 | 8/1965 | Lentze | 250/563 |
| 3,618,063 | 11/1971 | Johnson | 250/563 |
| 3,744,915 | 7/1973 | Sick | 356/386 |
| 3,866,054 | 2/1975 | Wolf | 250/562 |
| 3,919,531 | 11/1975 | Bobel et al. | 250/563 |
| 4,054,377 | 10/1977 | Gibson | 250/563 |

*Primary Examiner*—Stephen C. Buczinski
*Attorney, Agent, or Firm*—Townsend and Townsend

[57] ABSTRACT

The optical apparatus basically comprises a cylindrical lens which gathers light reflected at various angles from a material surface and projects it onto a strip like curved mirror with its axis at right angles to the lens and which subsequently concentrates the light onto a number of photodetectors each of which is associated with a specified range of angles. The light is projected onto the material surface by a scanning device.

The arrangement is such that the angle of reflection is determined irrespective of the point along the scanning line at which the scanned beam strikes the material surface.

Various arrangements of different types of photodetector devices are described including a matrix of photodetectors, light conducting rods with photodetectors arranged at their end faces and photomultipliers.

The apparatus is particularly suitable for monitoring the production of strip metal in strip mills to detect faults in the metal surface.

45 Claims, 8 Drawing Figures

OPTICAL APPARATUS FOR DETERMINING THE LIGHT EXIT ANGLE FROM A MATERIAL STRIP ILLUMINATED BY A LIGHT BEAD

The present invention relates to an optical apparatus for determining the light exit angle from a material strip, and has particular reference to an arrangement in which a strip of material is illuminated by a light bead, there being at least one photodetector and optical means arranged between the material strip and the photodetector to unite only those rays exiting from the light bead in a predetermined angular range at the photodetector, and wherein a cylindrical lens is arranged parallel to and spaced by its focal length from the material strip, the dimensions of the cylindrical lens being such that it receives all the light leaving the light bead within the range of light exit angles to be determined.

The term "light exit angle" will be understood to mean the angle at which light leaves a surface; the light could be reflected at the surface or transmitted therethrough, for example with refraction taking place.

It is already known (DE-OS 25 32 603) to arrange a stepped mirror arrangement parallel to a material strip swept over by a scanning light bead, the stepped mirror arrangement deflecting the light incident thereon onto various photodetectors of a matrix-like photodetection arrangement at the end face of a light conducting rod in dependence on the exit angle from the material strip. The known arrangement places, however, relatively strict requirements on the optical quality of the stepped mirror arrangement used and the light conducting rod. A further problem, that is especially pronounced when the light is incident on the parts of the light conducting rod that are a long way from the photodetectors, is that the light received is so scattered or deflected through inhomogeneities or other imperfections of the light conducting rod that it no longer falls on the photodetector which is intended to be associated with the angle at which it leaves the material strip.

A prime object of the present invention thus resides in providing an optical arrangement of the kind previously named which operates very accurately for low manufacturing and assembly costs and which enables, whilst using a scanning light bead, an accurate measurement of the range of light exit angles independently of the point of incidence of the light and in which a good light yield should be guaranteed.

The optical apparatus in accordance with the invention should especially also be suitable for the detection of surface faults in sheet metal strips manufactured by rolling in which grooves are present in form of naturally rolled tracks in the direction of movement of the rolled metal strip. These tracks should, however, not be indicated by the apparatus. Light deflected at various angles by scores or regular depressions or raised parts should, however, be capable of being used for a sensitive indication of such faults.

Other objects and advantages of the present invention will become clear from the subsequent disclosure and the scope of the appended claims.

According to the present invention there is provided optical apparatus for determining the light exit angle from a material strip illuminated by a light bead, said apparatus including at least one photodetector and optical means disposed between the material strip and the photodetector and operative to unite light rays leaving the strip within a predetermined spatial angular range at the photodetector; the optical means comprising a cylindrical lens arranged parallel to and spaced substantially by its focal length from the material strip, the cylindrical lens having dimensions such that it receives all the light leaving the strip within the rays of light exit angles to be determined, and at least a strip of a curved mirror arranged behind the cylindrical lens and extending parallel thereto with its axis at right angles to the axis of the cylindrical lens, said at least one photodetector being located generally in the focal plane of the curved mirror to receive light leaving the strip within the predetermined spatial angular range and concentrated by said optical means on the photodetector.

Generally it will be desirable to determine more than a single spatial angular range and thus there will generally be provided at least one photodetector associated with each of the spatial angular ranges to be determined.

The curved mirror will generally be a cylindrical concave mirror hereinafter referred to simply as a cylindrical mirror because this can be relatively inexpensively manufactured.

The invention thus makes use of the fact that light leaving various points on a material strip arranged parallel to the cylindrical mirror at the same angles will be concentrated at a specific point in the focal plane, whilst light leaving the same point at different angles will be directed to different points in the focal plane. As specific types of faults on the surface of a material strip, especially a rolled sheet metal strip, reflect light incident from a specified direction at various angles in a wholly characteristic manner, specified types of faults can be detected independently of their position along the scanning track by processing the detected pattern in the focal plane through the detection device in a suitable manner.

In order that also the marginal regions of the material strip at the end of the scanning range of the scanning light bead can be detected without trouble or cost, the cylindrical mirror usefully projects at both sides beyond the cylindrical lens. In this connection the cylindrical mirror should project on both sides beyond the cylindrical lens by such an amount that, at the end of the cylindrical lens, light rays leaving the material strip at angles of from 10° to 20° and preferably 15° to the perpendicular still impinge on the cylindrical mirror. The region of from 10° to 20° is sufficient for recognizing all the required types of faults on sheet metal surfaces.

The cylindrical mirror is advantageously so tilted about its longitudinal axis that the reflected light passes sideways adjacent the cylindrical lens. In this way the two light beams upstream and downstream of the cylindrical mirror can be decoupled in simple fashion.

The cylindrical mirror should be arranged in general spaced apart by its focal length from the material strip which makes it possible to arrange the detection device, e.g., directly above the material strip. If one wishes to provide the detection device at a safe distance from the material strip the cylindrical mirror can, however, also be arranged at a greater distance from the material strip than its focal length.

To the extent that the optical apparatus operates with a light bead scanning the material strip transversely to its direction of movement the cylindrical lens should extend in manner known per se along the scanning region parallel to the scanning direction.

The detection device can in the simplest case be realized by arranging a matrix of photodetectors in the focal plane of the cylindrical mirror. The photodetectors should, however, preferably be photoelectric multipliers which as is known are relatively costly.

For this reason it is especially preferred in connection with the recognition of faults on the surface of rolled metal strips for at least one light conducting rod which is preferably round to be arranged to extend parallel to the longitudinal axis of the cylindrical mirror substantially at the focal plane of the cylindrical mirror. Should a light conducting rod be used then this is preferably arranged outside of the extended light bead present in the focal plane when the strip surface is undamaged so that the light conducting rod is working in the dark region.

In order, however, to achieve a sufficient differentiation between different types of fault a preferred embodiment utilizes three light conducting rods arranged parallel to and alongside one another the middle one of the light conducting rods being located at the position through which light from the undamaged material strip passes. At the ends of the light conducting rods mirror arrangements or photodetectors are provided in known manner. In the last named embodiment the signal received from the photodetector for the central light conducting rod can be used as a reference signal with which the signals received from the photodetectors of the neighbouring light conducting rods can be compared. In order to deflect the incident light as completely as possible into the light conducting rod there is preferably arranged in manner known per se before each light conducting rod a cylindrical lens extending parallel to the light conducting rod. The light conducting rods are preferably provided apart from this with the known stepped mirror arrangement on which the light is concentrated through the round shape of the light conducting rod and the cylindrical lens. In accordance with the invention, however, the stepped mirror arrangement does not need to be especially accurately manufactured because it does not play any roll in differentiating between angles but rather has the sole purpose of reflecting as much as possible of the light incident on the surface of the light conducting rod through angles of total reflexion into the light conducting rod.

In order to recognize uniform depressions or raised parts of the sheet metal surface an especially preferred embodiment uses deflecting mirrors arranged above the central region of the side light conducting rods which each reflect the light falling on them to a respective photodetector.

Whilst the photodetectors at the side light conducting rods make it possible to recognize scores on the strip surface which have a significant transverse component relative to the rolling direction, the two photodetectors which receive light from the deflecting mirrors determine the relevant raised parts or depressions in the strip surface.

To the extent that the scanning light bead is generated by means of a light deflection device such as a mirror wheel via a strip-like cylindrical mirror and a cylindrical lens it is useful for a part of the aperture of the cylindrical lens and the cylindrical mirror to be used for the transmitted light and the rest to be used for the light to be detected. The two relevant optical elements are thus used twice. In the simplest case the detection device lies adjacent the light deflecting device as seen from its rotational axis. To the extent that it is, however, desired to arrange the detection device at a position remote from the light deflecting device a further embodiment envisages that a ray deflection takes place between the light deflection device and the cylindrical mirror through mutually inclined plane mirrors and that the detection device is arranged at a distance from the light deflection device corresponding to the inclination of the mirrors.

The invention will now be described by way of example only and with reference to the accompanying drawings in which are shown.

Figure 1:
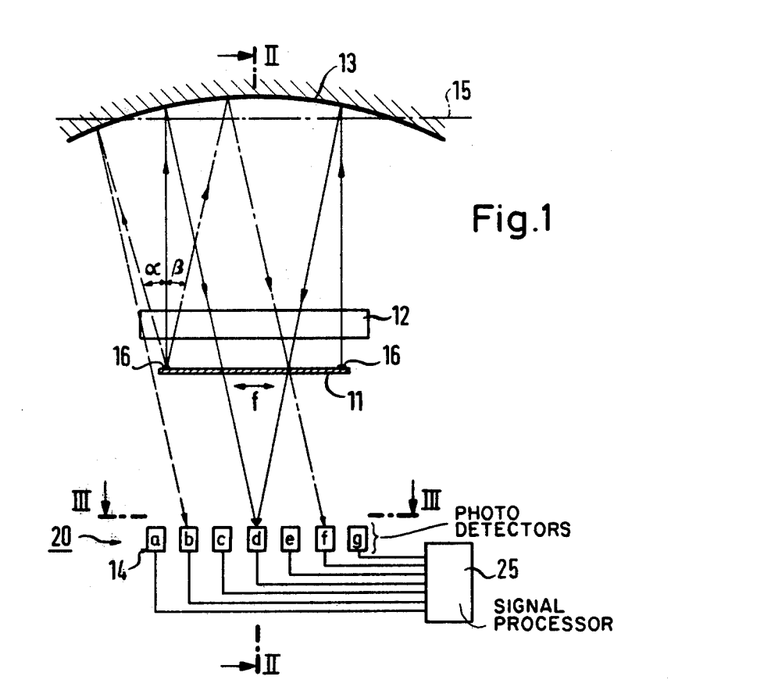
FIG. 1 a schematic side view of a preferred embodiment of the optical apparatus for determining the light exit angle, FIG. 2 a view in the direction II—II of FIG. 1, FIG. 3 a view in the direction III—III of FIG. 1, FIG. 4 a view similar to that of FIG. 1 but of a further advantageous embodiment, FIG. 5 a view similar to FIG. 2 of the embodiment of FIG. 4, FIG. 6 a view similar to FIG. 3 of the embodiment of FIG. 4, FIG. 7 a schematic view of a further embodiment of the optical apparatus in accordance with the invention in which some optical elements are used both for the transmitted and received ray path and FIG. 8 a schematic view similar to FIGS. 2 and 5 of a further especially advantageous embodiment.
Figure 2:
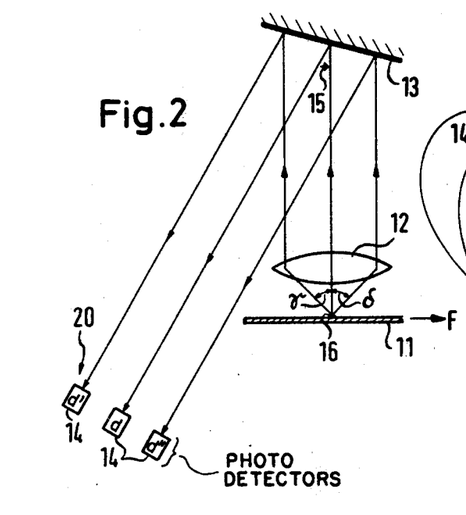
Figure 3:
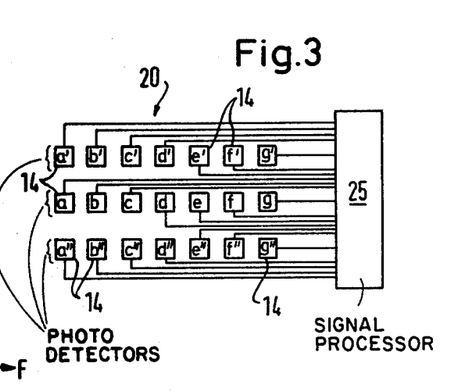

As seen in FIGS. 1 to 3 a sheet metal strip 11 moves in continuous fashion in the direction of the arrow F. The sheet metal strip can e.g. be a sheet metal strip issuing from a rolling mill. In the view shown in FIG. 1 the direction of movement F of the strip is at right angles to the plane of the drawing.

Figure 7:
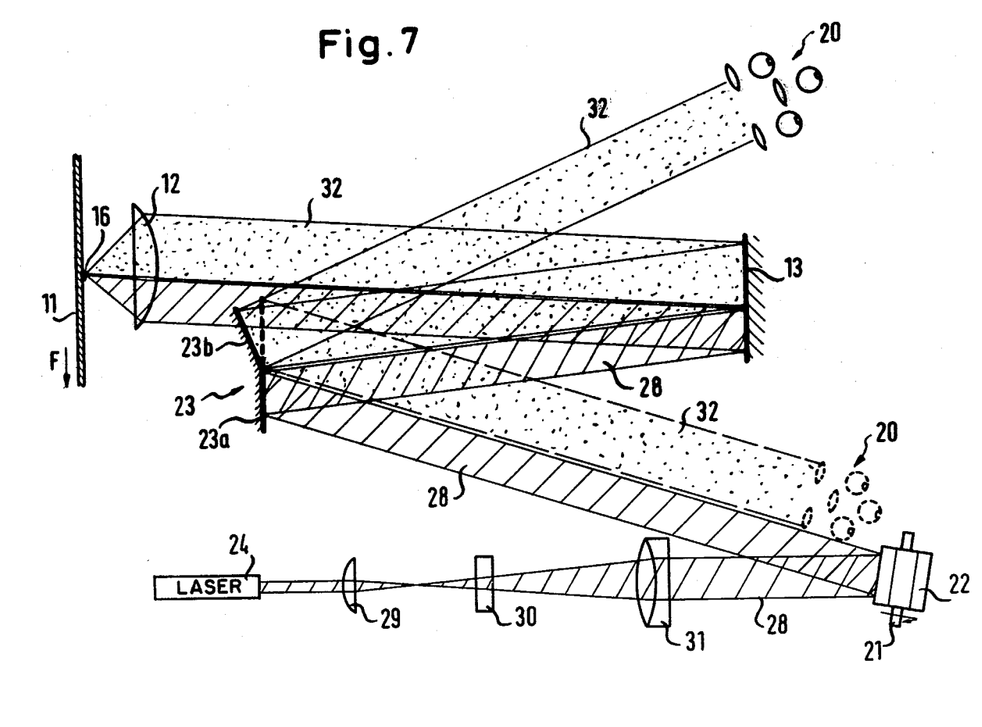

A small light bead 16 which can e.g. be generated by a laser 24 in accordance with the embodiment shown in FIG. 7, periodically scans the metal strip 11 over its entire width in the direction shown by the double arrow f of FIG. 1. The scanning speed and the speed of movement of the strip are so related one to the other that on taking into account the spatial extent of the small light bead 16 the entire surface of the material strip 11 is sequentially detected by the scanning light bead.

A cylindrical lens 12 the spacing of which from the material strip 11 is the same as the focal length of the lens extends parallel to the material strip 11. The line focus of the cylindrical lens 12 is thus located at the position of the scanning bead 16. The line focus substantially coincides with the line described by the scanning light bead 16.

A cylindrical mirror 13 is arranged at a considerably larger spacing from the strip 11 than the cylindrical lens 12 and the cylindrical axis of the cylindrical mirror is at right angles to the axis of the cylindrical lens. The cylindrical mirror 13 has the form of an elongate strip and its elongate direction is indicated at 15. The elongate direction 15 of the cylindrical mirror 13 extends parallel to the material strip 11 and to the axis of the cylindrical lens 12.

As seen in FIG. 2 the cylindrical mirror 13 is so tilted about its elongate direction 15 away from its position parallel to the material strip 11 that all the light rays gathered by the cylindrical lens 12 as per FIG. 2 are deflected past the cylindrical lens 12 to a detection device 20 which is provided at a distance equivalent to the focal length of the cylindrical mirror and which, in accordance with the embodiment of FIGS. 1 to 3 comprises a matrix arrangement of photodetectors 14a, b, c, . . . , a', b', c', . . . , a", b", c", . . . . The photodetectors are collectively connected via respective wiring to processing electronics 25 in which the detection signals can be combined together in each of the desired ways.

In FIG. 1 all the light leaving the material strip 11 at right angles is united at the central photodetector 14d. As the light bead 16 at a specified time only detects a specific point on the surface of the material strip 11 the incidence of light on the photodetector 14d shows that light from the light bead 16 is leaving the material strip 11 at right angles.

In FIG. 1 the light bead 16 is reproduced by way of example at two points on the surface of the material strip 11. In reality the light bead 16 impinges at both positions but never, however, at the same time but rather at sequential time points.

It is e.g. assumed in FIG. 1 that two further light rays merge at angles $\alpha$ and $\beta$ to the perpendicular direction from the light bead 16 shown on the left. These two further light rays fall respectively on the photodetectors 14b and 14f because of the arrangement of the invention and indeed irrespective of the actual position at which the light bead 16 is located on the material strip 11.

FIG. 2 shows how different light exit angles in the plane at right angles to FIG. 1 have the result that the light impinges on different photodetectors. Whilst the light ray shown in FIG. 2 leaving the material strip 11 at right angles impinges, as in FIG. 1, on the central photodetector 14d, rays assumed e.g. to be at angles $\gamma$ and $\delta$, respectively, reach the neighbouring photodetectors 14d' and 14d'', respectively. If the deflections in both planes were to be superimposed, e.g. the deflection $\alpha$ of FIG. 1 and the deflection $\gamma$ of FIG. 3 then the light received would also impinge on further photodetectors of the matrix arrangement of FIG. 3, in the above assumed example on the photoreceiver 14b'.

It is thus possible, in this manner, and depending on the resolution of the matrix arrangement to distinguish between different spatial angular ranges of the light emerging from the scanning light bead 16 and, indeed, independently from the position of the scanning cycle at which the scanning light bead 16 is at that instant to be found.

The arrangement of a large number of photodetectors as shown in the embodiments of FIG. 1 to 3 can economically only be proposed when it is necessary to recognize a large number of different spatial angular ranges. In general, and indeed especially for the recognition of faults in rolled metal surfaces it is, however, sufficient when the angle between a few specified angular ranges can be differentiated. The arrangement of FIGS. 4 to 6 shows a detection device which is especially suitable for the recognition of surface faults in rolled sheet metals.

The detection device 20 comprises three light conducting rods 17a, b and c arranged parallel to one another which receive light from cylindrical lenses 18a, b and c which run parallel to the light conducting rods. The light conducting rods are provided with stepped mirror arrangements 26 at their surfaces diametrically opposite to the light inlet which deflects the light at angles of total reflexion into the light conducting rod in the manner shown in FIG. 4.

Figure 4:
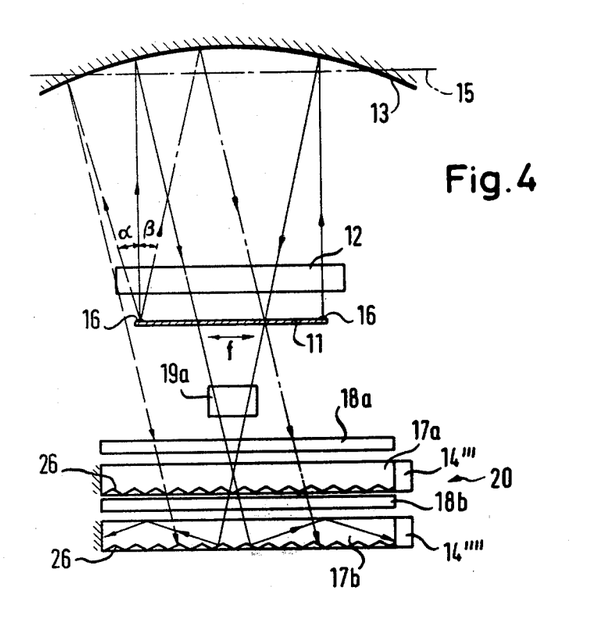
Figure 5:
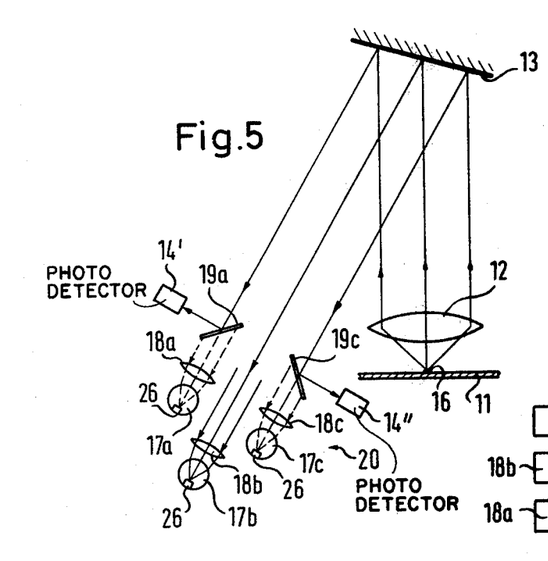

As seen in FIGS. 4 and 5 the light conducting rods 17a, 17c together with their associated cylindrical lenses 18a, and c are arranged at the same level whilst the central light conducting rod 17b together with its associated cylindrical lens 18b is arranged somewhat lower; this has constructional advantages. Through this displaced arrangement as shown in FIG. 4 and 5 it is possible to allow the ranges of reception of the three light conducting rods to border directly on one another without the light conducting rods or the cylindrical lenses having to contact one another. The displacement of the light conducting rods in the direction of the optical axis does not play a decisive roll for longer focal length of the cylindrical mirror 13.

Figure 6:
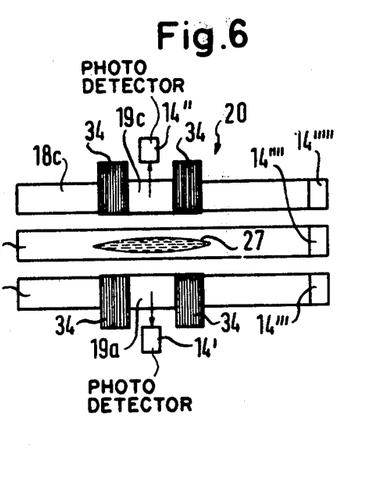

The light conducting rod arrangement of FIGS. 4 to 6 only makes it possible in the first place to distinguish between three different angular ranges in the plane of FIGS. 2 to 5 but this is, however, already sufficient for the recognition of scores. The central light conducting rod receives the light which appears in the focal plane of the cylindrical lens 13 when the material surface is undamaged. An extended elongate light bead 27 is used for rolled metal surfaces as schematically illustrated in FIG. 6. The scattered light represented within the light bead 27 originates from the natural grooves provided in the direction of movement of the strip 11. The elongate light bead brought about in this manner falls only on the central light conducting rod 17b so that the light reflected from the undamaged surface of the material strip 11 only falls on a single photodetector and indeed the photodetector 14'''' at the end face of the light conducting rod 17b. The corresponding electrical signal can be used as a reference size for the remaining output signals.

Scratches having a significant component transverse to the direction of movement of the strip 11 affect the side light conducting rods 17a and 17c and cause corresponding electrical signals at the photo 14''' or 14''''' at the respective end faces of these light conducting rods.

Rays leaving the strip 11 at the angles $\alpha$ and $\beta$ impinge, as seen in FIG. 4, on the same light conducting rod 17b so that, different angles are intentionally not distinguished in this plane.

As seen in FIGS. 4 to 6 flat deflecting mirrors 19a, 19c are arranged above the cylindrical lenses 18a, 18c essentially in the middle of the scanning range which deflect light incident on their surfaces outwardly to photodetectors 14' and 14''. The deflecting mirrors 19a, 19c extend over only a small proportion of the length of the light conducting rods 17. The deflecting mirrors only prevent light deflected out of the plane of FIG. 4 from impinging on the light conducting rods 17a, 17c in this region.

On the occurrence of depressions or raised parts of the material strip 11 having continuously falling or rising flanks, it turns out, that it is primarily the deflecting mirrors 19a, 19c which receive the light hereby deflected so that corresponding electrical signals are produced at the photodetectors 14', 14''.

As seen in FIG. 6 stops 34 can also be arranged on both sides of the defelcting mirrors 19a, 19c which have the effect that regions are present in a specified range between the deflecting mirrors 19 and the light conducting rods 17a and 17c through which no light reaches the light conducting rods. By this means a certain angular decoupling is achieved between the light which falls on the deflecting mirrors 19a, 19c and that which falls on the light conducting rods 17a and 17c. The extent of the stops 34 in the direction of the axis of the light conducting rods corresponds in order of magnitude to the corresponding extent of the deflecting mirrors 19.

The photodetectors 14' to 14''''' can be connected to a suitable processing electronics 25 in similar manner to the example of FIG. 1 to 3.

In the exemplary embodiment shown in FIG. 7 the optical apparatus and the detection device 20 correspond to the exemplary embodiment of FIGS. 4 to 6. The cylindrical mirror 13 and the cylindrical lens 12 are, however, simultaneously used for generating the scanning light bead 16 by utilizing a part of their apertures transverse to the scanning direction for the transmitted ray 28. A laser 24 generates, via two crossed cylindrical lenses 29 and 30 provided for spreading the ray, a light beam which is directed as a parallel beam by the front objective 31. The transmitted light beam 28 generated in this manner is directed onto a plane mirror 23a by a mirror wheel 22, which is rotatable about an axis 21, and the plane mirror 23a projects the transmitted light beam onto the lower region of the cylindrical mirror 13 of FIG. 7. The cylindrical mirror 13 and the cylindrical lens 12 together concentrate the light beam onto the scanned light patch 16.

Two possibilities are shown in FIG. 7 for the arrangement of the detection device 20. In the one embodiment shown in full lines, the received beam 32 is directed via the cylindrical mirror 13 onto a plane mirror 23b arranged adjacent to the plane mirror 23a; the plane mirror 23b is tilted relative to the plane mirror 23a in the manner illustrated about an axis which is at right angles to the plane of FIG. 7. In this way the received beam 32 is deflected upwardly so that the detection device 20 can be arranged at a significant distance from the cylindrical mirror 13 and the mirror wheel 22.

A simplified embodiment is shown in broken lines in which only a single plane mirror 23 is provided for both beams; the plane mirror 23 reflects the transmitted light beam 28 to the cylindrical mirror 13 with its lower region whilst, in FIG. 7, the upper region deflects the received beam 32 to a detection device which lies adjacent to the mirror wheel 22 as seen in the direction of the axis 21. The last named embodiment is characterized by its particularly compact construction.

It is also possible to do away with the plane mirror 23 and to arrange the mirror wheel 22 together with the optical elements which supply light to the mirror wheel so that light reflected at the mirror wheel is deflected directly to the cylindrical mirror 13. In this case the detection device should likewise be arranged adjacent the mirror wheel as shown by broken lines in FIG. 7.

Figure 8:
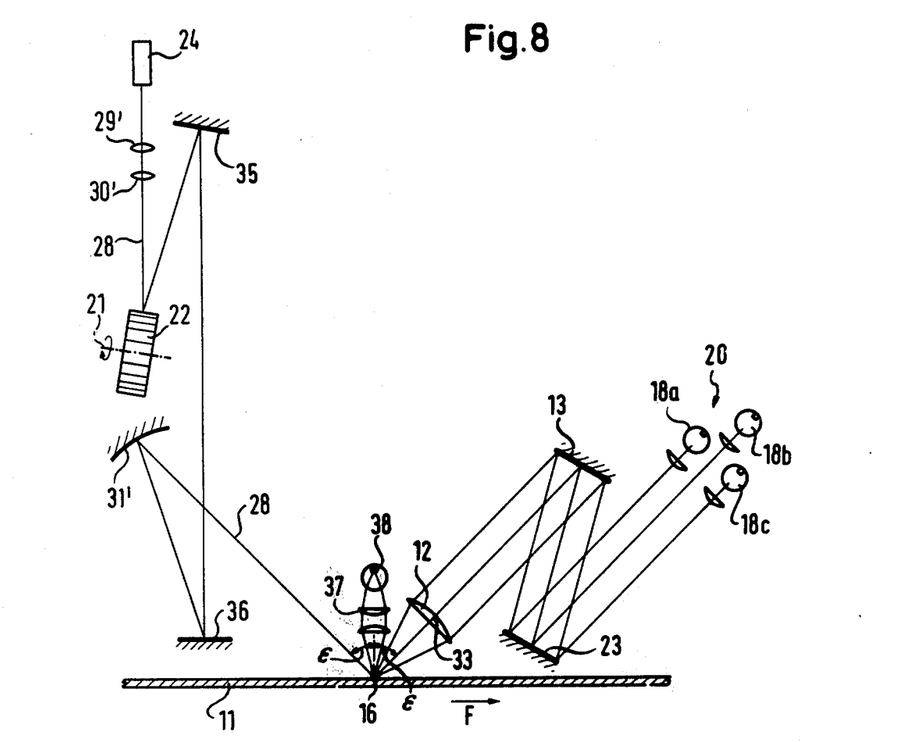

FIG. 8 illustrates particularly suitable transmission and detection apparatus for the recognition of surface faults in sheet metal strips 11.

A laser 24 generates via beam spreading optics 29′,30′ a sharply defined transmitted beam having a light bead in the range of approximately $0.1 \times 1$ mm to $1 \times 10$ mm. The beam is deflected by a mirror wheel 22 rotating about an axis 21 onto a plane mirror 35 from which it reaches a concave mirror 31′, which can be made spherical or parabolic and of strip form with its axis at right angles to the plane of the drawing, via a further plane mirror 36. Taking into account the double deflection at the mirrors 35, 36, which moreover are likewise of strip form and arranged at right angles to the plane of the drawing, the concave mirror 31′ is spaced by its focal length from the mirror wheel 22. The transmitted beam 28 is deflected from the concave mirror 31′ at an angle $\epsilon$ to produce the scanning light bead 16 on the sheet metal strip 11. The angle $\epsilon$ lies preferably between 10° and 80°. It is important that no further optical elements are located between the concave mirror 31′ and the scanning light bead 16. The size of the scanning light bead 16 lies in this manner approximately in the range of $0.1 \times 1$ mm to $1 \times 10$ mm. The distance between the concave mirror 31′ and the scanning light bead 16 lies between $\frac{1}{2}$ and 1/10 of the focal width of the concave mirror 31′.

The cylindrical lens 12 and its optical axis 33 arranged at the angle of reflexion $\epsilon$ of the transmitted beam 28. The light leaving the cylindrical lens is directed via the cylindrical mirror 13 arranged as in FIG. 8 and a plane mirror 23 onto the detection device 20 which is constructed once more in the form shown in FIG. 4 to 6.

As the cylindrical lens 12 is arranged at the angle of reflexion $\epsilon$ relative to the transmitted beam 28 the light reflected normally at the surface of the strip 11 reaches the central light conducting rod 18b practically in its entirety so that for rolled sheet metal the pattern 27 of FIG. 6 is generated. The detection device according to FIGS. 4 to 6 is thus preferably arranged at the angle of reflexion $\epsilon$ to the transmitted beam 28 as per FIG. 8.

Between the transmitted beam 28 and the cylindrical lens 12 there is located, practically perpendicularly above the strip, a cylindrical lens 37 behind which there is arranged a light conducting rod 38. Both elements run, like the cylindrical lens 12, parallel to the scanning direction. The light conducting rod 38 serves to receive the light remitted from the surface of the strip 11. This reception system is preferably used for recognizing flecks on the surface of the strip.

Other possible modifications to the apparatus disclosed and claimed will be apparent to those skilled in the art without departing from the scope of the present teaching, in particular the term photodetector will be understood to cover also photoreceivers such as photomultipliers in which, as an end result, photo detection takes place.

I claim:

1. Apparatus for determining the light exit angle at which light leaves a line illuminated point by point on a material surface, said optical apparatus comprising: a cylindrical lens arranged with its focal line substantially coincident with said illuminated light, the cylindrical lens having dimensions such that it receives all the light leaving the strip within the range of light exit angles to be determined; at least a strip of a concavely curved mirror curved in one plane and arranged optically downstream of the cylindrical lens and extending parallel thereto with its line focus at right angles to the line focus of the cylindrical lens; and a plurality of stationary detection means each having at least one light input surface located substantially within an image plane of the curved mirror, which image plane is spaced from the curved mirror by a distance substantially equal to its focal length, each input surface being associated with a distinct range of angles at which light leaves said material surface, and including an associated photodetector for converting received light into an electrical signal.

2. Apparatus according to claim 1 wherein the curved mirror projects beyond both ends of the cylindrical lens.

3. Apparatus according to claim 2 wherein the curved mirror extends beyond both ends of the cylindrical lens by such an amount that light rays leaving the material strip at angles in the range up to 20° still impinge on the curved mirror.

4. Apparatus according to claim 1 wherein the curved mirror is tilted relative to the cylindrical lens so that light received from the cylindrical lens and reflected by the curved mirror passes sideways adjacent the cylindrical lens.

5. Apparatus according to claim 1 wherein the curved mirror is spaced from the material strip by an amount substantially equal to its focal length.

6. Apparatus according to claim 5 wherein the focal length of the curved mirror is substantially the same as the length of the illuminated line.

7. Apparatus according to claim 5 wherein the focal length of the curved mirror is somewhat longer than the length of the illuminated line.

8. Apparatus according to claim 1 wherein the plurality of stationary detection means is defined by a matrix of photodetectors arranged in the image plane.

9. Apparatus according to claim 1 wherein the plurality of stationary detection means comprises a plurality of light conducting rods.

10. Apparatus according to claim 9 wherein the plurality of stationary detection means further comprises a plurality of deflecting mirrors and associated photodetectors.

11. Apparatus according to claim 9 wherein each light conducting rod has a round cross-section.

12. Apparatus according to claim 9 and comprising first, second and third light conducting rods arranged parallel to one another, the second rod defining a central light conducting rod located so that light leaving the material strip impinges thereon when the surface of the material strip is undamaged.

13. Apparatus according to claim 12 wherein a respective cylindrical lens is arranged in front of each light conducting rod and extends parallel thereto.

14. Apparatus according to claim 13 wherein the first and third light conducting rods define side light conducting rods and wherein deflecting mirrors are arranged above a central region of the side light conducting rods for deflecting light incident on their mirror surfaces onto respective photodetectors.

15. Apparatus according to claim 1 wherein the cylindrical lens is adapted to receive light leaving the surface of said material strip at a substantially oblique angle thereto.

16. Apparatus according to claim 1 including beam scanning apparatus for scanning a bead of light along the line.

17. Apparatus according to claim 16 wherein the beam scanning apparatus is adopted to illuminate the material surface at an angle in the range from 10° to 80°.

18. Apparatus according to claim 16 including means separating the beam paths of the beam scanning apparatus from the beam paths of the image forming apparatus defined by the cylindrical lens, the curved mirror and the stationary detection means.

19. Apparatus according to claim 18 wherein the beam paths of the beam scanning apparatus include the curved mirror and the cylindrical lens.

20. Apparatus according to claim 19 wherein the beam paths of the beam scanning apparatus includes first portions of the curved mirror and the cylindrical lens, and wherein second portions of the cylindrical lens and the curved mirror direct light to the stationary detection means.

21. Apparatus according to claim 20 wherein a plane mirror is provided in the beam paths of the beam scanning apparatus, the plane mirror having a first surface portion adopted to reflect the optical scanning beam and a second surface portion adopted to direct light to the stationary detection means.

22. Apparatus according to claim 21 wherein the second surface portion of the plane mirror is angled with respect to the first portion thereof.

23. Apparatus for determining the light exit angle from a material strip, the apparatus comprising: a light source; optical scanning means adapted to scan a beam of light from the light source along a line across the surface of the material strip with the scanned beam being of constant inclination to the surface within an angular range from about 10° to about 80°; image forming means including a cylindrical lens disposed above the surface of the strip and spaced therefrom with its line focus generally coincident with the line, and at least a strip of a concavely curved mirror curved in one plane and arranged optically behind the cylindrical lens and extending parallel thereto with its line focus at right angles to the line focus of the cylindrical lens so as to produce a spacial distribution of light in a zone optically spaced apart from the curved mirror by a distance substantially the same as its focal length in dependence on the angles at which the light leaves the surface of the material strip; means adapting the apparatus to separate the zone from the optical scanning means; and a plurality of stationary detection means arranged spaced apart in the zone, each said stationary detection means having at least one light input surface associated with a distinct range of angles at which light leaves said material surface and including an associated photodetector.

24. Apparatus according to claim 23 wherein the means adapting the optical apparatus to separate the zone from the optical scanning means comprises means for producing optical separation of the beam paths of the scanned beam and the beam paths within the image forming means.

25. Apparatus according to claim 24 wherein the means for separating the beam paths of the scanned beam from the beam paths within the image forming means comprises the arrangement of the optical scanning means as a self-contained system.

26. Apparatus according to claim 25 wherein the optical scanning means includes means for obliquely illuminating the material strip, and wherein the image forming means is adapted to receive light reflected from the material strip.

27. Apparatus according to claim 24 wherein a first part of the aperture of said cylindrical lens and of said curved mirror is used for the optical scanning beam, and wherein a second part of the aperture of the cylindrical lens and of said curved mirror is used for the image forming means, and wherein the optical scanning means comprises a light scanning element adapted to scan a beam of light from the light source with the light scanning element spaced from the concavely curved mirror by a distance substantially equal to its focal length.

28. Apparatus according to claim 23 wherein the light scanning element comprises a rotating mirror wheel.

29. Apparatus according to claim 23 wherein the curved mirror projects beyond both ends of said cylindrical lens.

30. Apparatus according to claim 29 wherein the curved mirror extends beyond both ends of said cylindrical lens by such an amount that light rays leaving the material strip at angles in the range up to 20° and passing through the ends of the cylindrical lens still impinge on the curved mirror.

31. Apparatus according to claim 28 wherein the curved mirror projects beyond both ends of the cylindrical lens by such an amount that light rays leaving the material strip at angles in the range up to 15° and passing through the ends of the cylindrical lens stlll impinge on said curved mirror.

32. Apparatus according to claim 23 wherein the curved mirror is tilted relative to the cylindrical lens so that light received from the cylindrical lens and reflected by the curved mirror passes sideways adjacent the cylindrical lens.

33. Apparatus according to claim 23 wherein the optical scanning apparatus scans the beam of light along a line transverse to the direction of movement of the material strip.

34. Apparatus according to claim 23 wherein the plurality of stationary detection means comprises a matrix of photodetectors.

35. Apparatus according to claim 23 wherein the plurality of stationary detection means comprises a plurality of light conducting rods extending parallel to the longitudinal direction of the curved mirror.

36. Apparatus according to claim 35 wherein the light conducting rod has a round cross-section.

37. Apparatus according to claim 35 comprising first, second and third light conducting rods arranged parallel to one another, the second rod defining a central light conducting rod located at a position through which light specularly reflected from the material strip passes.

38. Apparatus according to claim 35 wherein a respective cylindrical lens is arranged in front of and extends parallel to each light conducting rod.

39. Apparatus according to claim 36 wherein the central light conducting rod is displaced from the plane defined by the other light conducting rods generally away from the curved mirror.

40. Apparatus according to claim 35 wherein the plurality of stationary detection means further comprises in respect of at least one of the light conducting rods an arrangement of deflecting mirrors located relative to central regions of said at least one light conducting rods so that light incident on the mirror surfaces is deflected onto respective photodetectors.

41. Apparatus according to claim 25 wherein the optical scanning means comprises a source of laser light, beam spreading means, a mirror wheel disposed to scan light received from the beam spreader means onto a further strip-like, curved mirror spaced by its focal length from the mirror wheel and from which the scanned beam is subsequently reflected onto the material strip through an intermediate space of between $\frac{1}{2}$ to 1/10 of the focal length of the further curved mirror.

42. Apparatus according to claim 39 including stops disposed to the sides of the deflecting mirrors.

43. Apparatus according to claim 23 wherein the means adapting the optical apparatus to separate the zone from the optical scanning means is operative to place the zone alongside the optical scanning means.

44. Apparatus according to claim 23 wherein the means adapting the optical apparatus to separate the zone from the optical scanning means is operative to position the zone remote from the optical scanning means.

45. A method for determining the presence and nature of irregularities in a surface of a strip material comprising the steps of: scanning a light bead over a surface to thereby generate light beams reflected by the surface at relative angles of reflections which are a function of the condition of the surface at the location at which they are reflected, optically capturing the reflected light beams and directing substantially all light beams reflected by the surface at a plurality of predetermined angles to a like plurality of predetermined, spaced apart locations, sensing light beams directed to the plurality of predetermined locations, generating output signals from light beams spaced at the locations, and processing the output signals to determine the presence and nature of surface irregularities of the strip material.

* * * * *